United States Patent [19]

Nakashima et al.

[11] 4,259,316

[45] Mar. 31, 1981

[54] ORAL COMPOSITION FOR CARIES PROPHYLAXIS

[75] Inventors: Syozi Nakashima, Ninomiya; Tosiyuki Ozawa, Minamiashigara; Takashi Ujiie, Ninomiya; Takeshi Naganuma, Odawara; Satoshi Hayashi, Hiratsuka; Yoshihito Ochiai, Fujisawa, all of Japan

[73] Assignee: Lion Corporation, Tokyo, Japan

[21] Appl. No.: 79,801

[22] Filed: Sep. 28, 1979

[30] Foreign Application Priority Data

Jul. 31, 1979 [JP] Japan .................................. 54-97627

[51] Int. Cl.$^3$ ................................................ A61K 7/18
[52] U.S. Cl. ....................................................... 424/52
[58] Field of Search ........................................... 424/52

[56] References Cited

U.S. PATENT DOCUMENTS 3,934,002  1/1976  Haefole .................................. 424/54

FOREIGN PATENT DOCUMENTS 1222197  2/1971  United Kingdom ...................... 424/52
1334375  2/1975  United Kingdom ...................... 424/52
1408922  10/1975  United Kingdom .................... 424/52

*Primary Examiner*—Shep K. Rose
*Attorney, Agent, or Firm*—Birch, Stewart, Kolasch & Birch

[57] ABSTRACT

An oral composition for caries prophylaxis which comprises 0.04 to 10% by weight of stannous fluoride and not less than 0.1% by weight of a phytic acid compound, the molar ratio of the phytic acid compound to stannous fluoride being in the range of from 0.01:1 to 4:1 and the composition being acidic, is effective in inhibiting dental caries and shows a prolonged effect after application. The oral composition may be used as mouthwashes, oral bands, topical solutions, cavity sealers, prophylactic pastes, dentifrices, dental flosses and the like.

5 Claims, No Drawings

ORAL COMPOSITION FOR CARIES PROPHYLAXIS

BACKGROUND OF THE INVENTION

This invention relates to oral compositions for use as dentifrices, topical solutions or pastes, disintegratable tablets, oral bands, cavity sealers, gels for ultrasonic treatment, gels for iontophoresis, prophylactic pastes, dental flosses, desensitizers of teeths, mouthwashes in the form of liquids, tablets, powders or gels, chewing gum and the like. More particularly, this invention relates to oral compositions containing stannous fluoride and a phytic acid compound such as phytic acid, its alkali metal or alkaline earth metal salts and phytin which are effective dental caries inhibitors capable of increasing the acid resistance of the tooth enamel upon application.

Various compounds have been proposed as effective ingredients for inhibiting dental caries. In particular, water-soluble fluoride compounds are known as being effective in inhibiting dental caries. When fluoride compounds are applied to a tooth surface, fluorine is taken up by the tooth enamel to enhance the acid resistance of the tooth enamel. Among such fluoride compounds most widely used are sodium monofluorophosphate, sodium fluoride and stannous fluoride. These compounds, however, are not fully effective to inhibit dental caries. Fluoride compounds containing stannous ions, for example, stannous fluoride, are proved as being more effective in improving the acid resistance of the tooth enamel than those containing no stannous ions, for example, sodium fluoride. These water-soluble stannous ion-containing fluoride compounds are effective to some extent, but their efficacy is not found to be very high. Further, the increased acid resistance of the tooth enamel is kept for only a limited period of time after treatment because the efficacy relatively readily disappears out as a result of the self-cleansing action of saliva, brushing, mastication and the like. Moreover, the stannous ion-containing fluoride compounds are chemically unstable.

In addition to fluoride compounds, a number of compounds have been investigated on their dental caries inhibition. One approach uses sodium or calcium phytate alone to reduce the solubility of hydroxyapatite in an acid, but has not generally been evaluated as sufficiently effective. Other examples using phytic acid are British Pat. No. 1,384,375 which discloses an oral hygiene composition comprising a divalent metal salt of phytic acid such as calcium phytate mixed with a monofluorophosphate, and British Pat. No. 1,408,922 which discloses an oral composition comprising two phases which are isolated from one another and/or do not react with one another, one phase containing a water-soluble calcium compound and the other phase containing a water-soluble organic or inorganic phosphoric acid compound such as phytic acid and optionally, a water-soluble fluoride compound. However, the evaluation of these compositions has not been widely established.

SUMMARY OF THE INVENTION

A primary object of this invention is to provide an oral composition which renders the tooth enamel highly resistant to acid even when applied at room temperature and hence has an improved dental caries inhibiting activity.

Another object of this invention is to provide an oral composition capable of keeping its efficacy for an extended period of time after application.

Briefly, this invention provides an oral composition for caries prophylaxis which comprises stannous fluoride and a phytic acid compound. The content of stannous fluoride is 0.04 to 10% by weight, the content of the phytic acid compound is 0.1% by weight or more, preferably 0.3 to 20% by weight of the composition, and the molar ratio of the phytic acid compound to stannous fluoride is in the range of from 0.01:1 to 4:1, more preferably 0.02:1 to 3:1. And the composition is acidic.

Application of the present composition, which contains stannous fluoride in admixture with a phytic acid compound, within the above-prescribed ranges of their contents and the relative molar ratio of the phytic acid compound and stannous fluoride, to a tooth surface substantially enhances the acid resistance of the enamel. This improvement is outstanding as compared with the cases where stannous fluoride or a phytic acid compound is applied alone, and where a phytic acid compound is applied in combination with sodium fluoride or sodium monofluorophosphate. Therefore, the composition of this invention is more effective for the inhibition of dental caries.

In a preferred embodiment of this invention, the contents of stannous fluoride and the phytic acid compound are 0.3 to 4% by weight and 0.5 to 10% by weight of the total composition, respectively, and the molar ratio of the phytic acid compound to stannous fluoride is in the range of from 0.025:1 to 2.5:1. The preferred composition has a pH of 2 to 6, specifically 2 to 5.5. These compositions give an unexpectedly high acid resistance to the tooth enamel.

The above and other objects, features and advantages of this invention will become more apparent and understandable from the following detailed description, examples and claims.

DETAILED DESCRIPTION OF THE INVENTION

The phytic acid compounds which can be used in the present invention in combination with stannous fluoride include phytic acid, alkali metal and alkaline earth metal salts of phytic acid in which one or more hydrogen atoms in the phosphate groups at the 1- to 6-positions of phytic acid are replaced by metal substituents, for example, sodium phytate, potassium phytate, lithium phytate, magnesium phytate, calcium phytate and phytin. Also included is ammonium phytate. These phytic acid compounds may be used singly or in combination.

More preferably, the phytic acid compound is selected from the group consisting of phytic acid, sodium phytate, potassium phytate, lithium phytate, ammonium phytate and mixtures thereof.

The phytic acid compound should be present in an amount of 0.1% (by weight: it is to be noted that percents are by weight hereinafter.) or more of the total composition so as to give 0.01 to 4 moles of the phytic acid compound per mole of stannous fluoride. Within this range, a high acid resistance is given to the tooth enamel and stannous fluoride is stabilized in the composition. Without any phytic acid compound, or when the phytic acid compound is added in amounts outside the above-prescribed content and molar ratio ranges, the resulting compositions are less effective so that the object of this invention cannot be achieved. For the purpose of further enhancing the acid resistance of the tooth enamel treated and the stability of stannous fluoride, the molar ratio of the phytic acid compound to stannous fluoride may preferably be 0.02:1 to 3:1, especially 0.025:1 to 2.5:1, and the content of the phytic acid compound may preferably be 0.3 to 20%, especially 0.5 to 10%. Contents of the phytic acid compound of more than 20% adversely affect the efficacy of the composition and are thus undesirable.

According to this invention, stannous fluoride may preferably be added in an amount of 0.04% or more, especially 0.1% or more in order to exhibit the satisfactory action of stannous ions. The upper limit of the stannous fluoride content is 10%. Stannous fluoride may be added in amounts exceeding its saturation level of solubility. At particular proportions between stannous fluoride and the phytic acid compound, particularly when the amount of the phytic acid compound is relatively smaller as compared with stannous fluoride, there often occurs precipitation, which causes no problem. An improved acid resistance can be imparted to the tooth enamel either in the presence or in the absence of a precipitate insofar as the contents and the relative molar ratio of the phytic acid compound and stannous fluoride fall within the above-prescribed ranges. The most preferred content of stannous fluoride is 0.1 to 4%, particularly 0.3 to 4% of the total composition.

An outstandingly high acid resistance is obtained when the oral composition comprises 0.3 to 4% of stannous fluoride and 0.5 to 10% of the phytic acid compound, the molar ratio of the phytic acid compound to stannous fluoride is in the range of from 0.025:1 to 2.5:1, and the composition has a pH of 2 to 5.5

The application forms of the oral composition according to this invention include dentifrices, topical solutions or pastes, disintegratable tablets, oral bands, cavity sealers, gels for ultrasonic treatment, gels for iontophoresis, prophylactic pastes, dental flosses, desensitizers of teeth, mouthwashes in the form of liquids, tablets, powders and gels, chewing gum and the like. In these oral compositions, commonly used ingredients in addition to stannous fluoride and the phytic acid compound may be added. In general, stannous fluoride, the phytic acid compound and any optical ingredients are blended in water to prepare an oral composition.

Liquid mouthwashes and topical solutions, for example, may be prepared by adding stannous fluoride and the phytic acid compound to a suitable solvent such as distilled or deionized water and ethanol. Sweetening agents such as saccharine, etc., and flavoring agents such as peppermint oil, spearmint oil, anise oil, etc. may also be added in a small amount, if desired. Gel-type mouthwashes and topical pastes may be prepared by adding to the above-prepared solution a humectant such as glycerin, sorbitol, propylene glycol and polyethylene glycol in an amount of 5–70 wt%, a binder such as xanthan gum, guar gum, carrageenan and sodium carboxymethyl cellulose in an amount of 0.3–10 wt %, and an antiseptic agent such as ethyl parahydroxybenzoate and butyl parahydroxybenzoate in a minor amount. Further, tablets and powders may be prepared in a usual manner using well-known tablet or powder-forming agents, for example, a vehicle such as lactose and mannitol, a disintegrator and a binder such as corn starch and carboxymethyl cellulose.

Oral bands may be prepared by dissolving or dispersing in water stannous fluoride and the phytic acid compound together with necessary components, for example, a tacky high-molecular substance soluble in water or changing into a gel in water such as sodium carboxymethyl cellulose, methyl cellulose, hydroxyethyl cellulose, hydroxypropyl cellulose, polyvinyl alcohol, polyvinylpyrrolidone, sodium polyacrylate, sodium alginate, dextran, gelatin, carrageenan and the like in a usual blending amount of 20–99 wt%; a polyhydric alcohol such as polyethylene glycol, propylene glycol, sorbitol, glycerin and the like in a usual blending amount of 1–50 wt%; and a surface-active agent such as an anionic active agent and a nonionic active agent (e.g. polyoxyethylene stearate or polyoxyethylene sorbitan monooleate) in a usual blending amount of 0–30 wt%. The resulting solution or dispersion is freeze dried to remove water and to form a film which may be cut into a desired shape.

Dentifrices may include an abrasive such as calcium pyrophosphate, insoluble alkali metal metaphosphates (e.g. insoluble sodium metaphosphate), titanium dioxide, resins, aluminum hydroxide, silicic anhydride, alumina-silicate and the like in a usual blending amount of 20–60 wt%; a binder such as xanthan gum, guar gum, carrageenan, hydroxyethyl cellulose, sodium carboxymethyl cellulose and the like in a usual blending amount of 0.5–5 wt%; a humectant such as glycerin, sorbitol and other polyhydric alcohols in a usual blending amount of 15–40 wt%; a forming agent such as water-soluble salts of the higher alkyl sulfates having 8 to 18 carbon atoms in the alkyl group (e.g. sodium lauryl sulfate), water-soluble salts of sulfonated monoglycerides of higher fatty acids having 10 to 18 carbon atoms in the fatty acid group (e.g. sodium coconut monoglyceride sulfonate), salts of amides of higher fatty acids having 12 to 16 carbon atoms in the fatty acid group with lower aliphatic amino acids (e.g. sodium-N-methyl-N-palmitoyl tauride or sodium N-lauroyl sarcosinate), sucrose fatty acid esters having 12 to 18 carbon atoms in the fatty acid group (e.g. sucrose monolaurate), condensates of sorbitan monostearate with approximately 60 moles of ethylene oxide, condensates of ethylene oxide with propylene oxide condensates of propylene glycol and the like in a usual blending amount of 0.5–3 wt%; a sweetening agent; a flavoring agent; an antiseptic agent; an anticariogenic agent such as chlorohexidine; and any other ingredients.

The oral composition of this invention is acidic. The pH of the composition may fall within the range of 2–6, more preferably 2–5.5 in order to exhibit the best effect from the composition. The acidity may be adjusted by the phytic acid compound. Alternatively, the acidity may be adjusted to a desired level by adding an organic acid such as citric acid, tartaric acid, lactic acid, malonic acid, malic acid, L-ascorbic acid, acetic acid, and succinic acid or alkali metal salts thereof, an inorganic acid such as hydrochloric acid and phosphoric acid, or an alkali such as sodium hydroxide.

It is to be noted that the composition of this invention may include sodium fluoride, potassium fluoride, sodium monofluorophosphate and other fluorides in addition to the essential stannous fluoride.

The oral composition of this invention may be used in an ordinary manner depending upon its type and form. For example, mouthwashes in the form of liquids may be applied with or without dilution with water while those in the form of tablets, powders or gels may be applied after they are dissolved or dispersed in water. Oral bands may be attached to teeth. Then the high-molecular substance which is the main component of the band is gelated and becomes tacky upon contact with saliva. With the tacky band firmly adhered to the teeth, the active ingredients (stannous fluoride and the phytic acid compound) in the band act on the teeth. A topical solution or gel may be directly applied to a tooth surface.

As described above, the oral composition of this invention is applied to teeth directly or after it is prepared into a form suitable for oral application by diluting with, dissolving in or dispersing in water. Upon application to a tooth surface, stannous fluoride and the phytic acid compound contained at the above-prescribed contents and relative molar ratio in the composition exhibit a synergistic effect on the tooth enamel, thereby substantially enhancing the acid resistance of the tooth enamel. The oral composition of this invention can be applied at room temperature or approximately 30° C. without a reduction in the acid resistance improvement. Further, the efficacy after application is retained for an extended period of time. It was found that the acid resistance of the tooth enamel treated with the present composition remains high even after the tooth is washed with running tap water for 24 hours. It was also found that stannous ions are stable in the composition for a long period of storage. This means that the present composition is an effective dental caries inhibitor which can be stored for an extended period of time and shows a prolonged activity after application.

The following examples are further illustrative of the present invention, but it is to be understood that the invention is not limited thereto. All percents in the examples are percents by weight unless otherwise specified.

EXAMPLE 1

Stannous fluoride and pentasodium phytate represented by the formula:

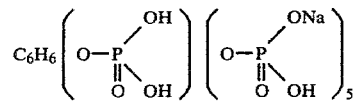

were added to water in given amounts. Hydrochloric acid or sodium hydroxide aqueous solution was added to adjust the pH thereof, obtaining a number of test solutions varying in stannous fluoride content, pentasodium phytate content, pentasodium phytate/stannous fluoride molar ratio, and pH.

An enamel block made of a bovine enamel (incisor) was immersed for 3 minutes in each of the test solutions at 30° C. Each block was brushed twenty times, that is, ten times in each of the longitudinal and transverse directions with a toothbrush. For the purpose of determining the retention of the activity, the treated enamels were allowed to stand in tap water at 37° C. for 20 hours. Thereafter, the thus treated enamels were subjected to decalcification in an acidic solution (buffered solution of 0.1 M acetate at pH 4.5) at 20° C. for 2 hours. After decalcification, the surface hardness (Vickers hardness number: VHN) was measured on the enamel surface of each enamel block to evaluate the effect of the test solution on the acid resistance of the enamel.

After the test solutions prepared as above were stored for 1 month at 40° C., the above test procedure was repeated to determine the acid resistance for evaluation of the stability of the solutions under storage.

For comparison, enamel blocks were treated with aqueous solutions containing varying amounts of stannous fluoride at pH 3.0 and aqueous solutions containing varying amounts of pentasodium phytate at pH 3.0, respectively. After the blocks were subjected to decalcification, the Vickers hardness was measured in the same manner as above.

The results are shown in Tables 1 and 2. Each hardness value in the Tables is an average of 15 measurements.

It should be noted that the acid-resistance evaluation for the tooth enamel including the decalcification under the above-described conditions followed by hardness measurement is a very severe one because the samples treated with 8% $SnF_2$ in water were decalcified to a considerable extent in the above-mentioned decalcifying solution. Accordingly, hardnesses above 150, particularly above 200 indicate a considerable improvement in acid resistance. Oral compositions resulting in such high hardnesses are very effective in inhibiting dental caries.

Symbols in the "Stability" column in the Tables have the following meanings. The stability of the test solutions under storage was evaluated by comparing the effect on the increment of the acid-resistance by a test solution stored at 40° C. for 1 month with that by an initial test solution.

o: Retention of efficacy of a stored test solution is 80% or more.

Δ: Retention of efficacy is 65% or more.

X: Retention of efficacy is less than 65%.

In the following Tables, P*-5Na is pentasodium phytate, and "u.m." is the abbreviation of "unmeasurable" which means that hardness measurement is impossible because of destruction of a tooth surface by decalcification (Vickers hardness is less than 50) under the above-described severe test conditions.

TABLE 1

| | | (Test solutions at pH 3.0) | | | | |
|---|---|---|---|---|---|---|
| Content of $SnF_2$ (%) | Content of $F^-$ (ppm) | Content of P*-5Na (%) | P*-5Na/$SnF_2$ (molar ratio) | VHN | Stability | |
| | | 0 | 0 | u.m. | X | Comparison |
| | | 0.02 | 0.1 | 103 | X | " |
| 0.04 | 97 | 0.05 | 0.25 | 125 | X | " |
| | | 0.1 | 0.5 | 155 | Δ | The invention |
| | | 0.4 | 2.0 | 166 | Δ | " |
| | | 0.6 | 3.0 | 152 | O | " |
| | | 0 | 0 | u.m. | X | Comparison |
| | | 0.3 | 0.3 | 162 | Δ | The invention |
| 0.2 | 490 | 0.5 | 0.5 | 180 | Δ | " |
| | | 1.0 | 1.0 | 220 | O | " |

TABLE 1-continued (Test solutions at pH 3.0)

| Content of SnF$_2$ (%) | Content of F$^-$ (ppm) | Content of P*-5Na (%) | P*-5Na/SnF$_2$ (molar ratio) | VHN | Stability | |
|---|---|---|---|---|---|---|
| | | 2.0 | 2.0 | 206 | O | " |
| | | 3.0 | 3.0 | 147 | O | " |
| | | 0 | 0 | 90 | X | Comparison |
| | | 0.5 | 0.25 | 188 | Δ | The invention |
| 0.4 | 970 | 1.0 | 0.5 | 215 | O | " |
| | | 2.0 | 1.0 | 260 | O | " |
| | | 4.0 | 2.0 | 271 | O | " |
| | | 5.0 | 2.5 | 220 | O | " |
| | | 6.0 | 3.0 | 174 | O | " |
| | | 10.0 | 5.0 | 133 | O | Comparison |
| | | 0 | 0 | 83 | X | Comparison |
| | | 0.3 | 0.05 | 153 | Δ | The invention |
| | | 0.5 | 0.08 | 196 | O | " |
| 1.2 | 3000 | 0.8 | 0.136 | 240 | O | " |
| | | 1.0 | 0.17 | 253 | O | " |
| | | 1.5 | 0.25 | 263 | O | " |
| | | 3.0 | 0.5 | 283 | O | " |
| | | 6.0 | 1.0 | 297 | O | " |
| | | 12.0 | 2.0 | 196 | O | " |
| | | 15.0 | 2.5 | 156 | O | " |
| | | 0 | 0 | 95 | X | Comparison |
| | | 0.5 | 0.025 | 222 | O | The invention |
| | | 1.0 | 0.05 | 235 | O | " |
| 4.0 | 10000 | 2.0 | 0.1 | 230 | O | " |
| | | 5.0 | 0.25 | 253 | O | " |
| | | 10.0 | 0.5 | 207 | O | " |
| | | 15.0 | 0.75 | 188 | O | " |
| | | 20.0 | 1.0 | 186 | O | " |
| | | 0 | 0 | 104 | X | Comparison |
| | | 0.5 | 0.01 | 163 | Δ | The invention |
| | | 1.0 | 0.02 | 187 | O | " |
| 10 | 25000 | 2.0 | 0.04 | 207 | O | " |
| | | 5.0 | 0.1 | 233 | O | " |
| | | 10.0 | 0.2 | 258 | O | " |
| | | 15.0 | 0.3 | 213 | O | " |
| | | 20.0 | 0.4 | 208 | O | " |
| | | 0 | — | u.m. | — | Comparison |
| 0 | 9047 | 1 | — | u.m. | — | " |
| | (2% NaF) | 2 | — | u.m. | — | " |
| | | 5 | — | u.m. | — | " |
| | | 0 | — | u.m. | — | Comparison |
| 0 | 0 | 1 | — | u.m. | — | " |
| | | 2 | — | u.m. | — | " |
| | | 5 | — | u.m. | — | " |
| 0 | 1000 (0.76% Sodium monofluorophosphate) | 1.0 | — | u.m. | — | Comparison (test solution at pH 7.0) |

TABLE 2

| P*-5Na/SnF$_2$ (molar ratio) | Content of SnF$_2$ (%) | Content of P*-5Na (%) | pH | VHN |
|---|---|---|---|---|
| 0.25 | 1.2 | 1.5 | 2 | 272 |
| | | | 3 | 263 |
| | | | 4 | 238 |
| | | | 5 | 221 |
| 0.5 | 1.2 | 3.0 | 2 | 288 |
| | | | 3 | 283 |
| | | | 4 | 256 |
| | | | 5 | 228 |
| 1.0 | 0.4 | 2.0 | 2 | 278 |
| | | | 3 | 260 |
| | | | 4 | 228 |
| | | | 5 | 219 |
| | 1.2 | 6.0 | 2 | 311 |
| | | | 2.5 | 308 |
| | | | 3 | 297 |
| | | | 3.5 | 263 |
| | | | 4 | 236 |
| | | | 5 | 198 |
| 2.0 | 0.4 | 4.0 | 2 | 268 |
| | | | 3 | 271 |
| | | | 4 | 226 |
| | | | 5 | 196 |

EXAMPLE 2

Test solutions were prepared by adding 1.2% by weight of stannous fluoride and a given amount of pentapotassium phytate, pentamagnesium phytate or pentacalcium phytate to water. Hydrochloric acid or sodium hydroxide aqueous solution was added to the test solutions to adjust the pH thereof.

The test procedure described in Example 1 was repeated to evaluate the acid resistance of enamel blocks treated with the test solutions.

The results are shown in Table 3.

TABLE 3

| Phytate | Content (%) | Vickers hardness at solution pH | | |
|---|---|---|---|---|
| | | 3.0 | 4.0 | 5.0 |
| Pentapotassium phytate | 5 | 305 | 230 | 183 |
| Pentamagnesium phytate | 1 | 240 | 160 | 120 |
| Pentamagnesium phytate | 5 | 250 | 164 | 132 |
| Pentacalcium phytate | 1 | 166 | 121 | 70 |
| Pentacalcium phytate | 5 | 150 | 127 | 68 |

As shown in Tables 1–3, a specific combination of stannous fluoride with the phytic acid compound, where the contents of stannous fluoride and the phytic acid compound are 0.04 to 10% and not less than 0.1% by weight, respectively, and the molar ratio of the phytic acid compound to stannous fluoride is in the range of from 0.01:1 to 4:1, provides a significant improvement in the acid resistance of tooth enamel as compared with the use of a single component, stannous fluoride or the phytic acid compound, or a combination of sodium fluoride and the phytic acid compound or other prior art oral compositions. More particularly, when the content of the phytic acid compound is 0.3 to 20%, specifically 0.5 to 10% by weight and the molar ratio of the phytic acid compound to stannous fluoride is in the range of from 0.02:1 to 3:1, specifically from 0.025:1 to 2.5:1, the acid resistance of tooth enamel is remarkably improved. Even after the treated enamel is washed with running tap water for 20 hours, the acid resistance provided by the composition of this invention is kept high. This means that the effect is retained for an extended period of time.

EXAMPLE 3

| Dentifrice | |
|---|---|
| Insoluble sodium metaphosphate | 40.0% |
| Silicic anhydride | 3.0% |
| Propylene glycol | 3.0% |
| Glycerin | 10.0% |
| Sorbitol | 10.0% |
| Xanthan gum | 0.5% |
| Carboxymethyl cellulose | 0.6% |
| Sodium lauryl sulfate | 2.0% |
| Flavor | 0.5% |
| Saccharin | 0.1% |
| Butyl parahydroxybenzoate | 0.01% |
| Stannous fluoride | 0.4% |
| Pentasodium phytate | 2.5% |
| Water | Balance |
| | 100.0% |

Stannous fluoride and pentasodium phytate were dissolved in some of the water. In order to prepare a dentifrice, this solution was mixed with the paste obtained by blending the other ingredients with the remaining water.

EXAMPLE 4

| Dentifrice | |
|---|---|
| Stannous fluoride | 0.41% |
| Phytic acid | 2.5% |
| Malonic acid | 0.31% |
| Insoluble sodium metaphosphate | 40.0% |
| Propylene glycol | 3.0% |
| Glycerin | 10.0% |
| Sorbitol | 5.0% |
| Hydroxyethyl cellulose | 1.5% |
| Sodium lauryl sulfate | 2.0% |
| Flavor | 0.5% |
| Saccharin | 0.1% |
| Butyl parahydroxybenzoate | 0.01% |
| Water | Balance |
| | 100.0% |

A dentifrice was prepared as in Example 3.

EXAMPLE 5

| Dentifrice | |
|---|---|
| Calcium pyrophosphate | 40.0% |
| Propylene glycol | 3.0% |
| Glycerin | 10.0% |
| Sorbitol | 5.0% |
| Guar gum | 0.5% |
| Carrageenan | 0.5% |
| Sodium lauryl sulfate | 1.0% |
| Saccharose monolaurate | 1.5% |
| Flavor | 0.5% |
| Saccharin | 0.1% |
| Butyl parahydroxybenzoate | 0.01% |
| Stannous fluoride | 0.2% |
| Sodium fluoride | 0.11% |
| Pentasodium phytate | 1.0% |
| Water | Balance |
| | 100.0% |

A dentifrice was prepared as in Example 3.

EXAMPLE 6

| Dentifrice | |
|---|---|
| Silicic anhydride | 25.0% |
| Propylene glycol | 3.0% |
| Glycerin | 8.0% |
| Sorbitol | 12.0% |
| Hydroxyethyl cellulose | 3.0% |
| Sodium lauryl sulfate | 1.5% |
| Flavor | 0.5% |
| Saccharin | 0.2% |
| Butyl parahydroxymbenzoate | 0.01% |
| Stannous fluoride | 0.4% |
| Pentapotassium phytate | 2.5% |
| Water | Balance |
| | 100.0% |

A dentifrice was prepared as in Example 3.

EXAMPLE 7

| Dentifrice | |
|---|---|
| Insoluble sodium metaphosphate | 40.0% |
| Propylene glycol | 3.0% |
| Glycerin | 4.0% |
| Sorbitol | 12.0% |
| Xanthan gum | 1.2% |
| Sodium lauryl sulfate | 2.0% |
| Flavor | 0.5% |
| Saccharin | 0.1% |
| Butyl parahydroxybenzoate | 0.01% |
| Stannous fluoride | 0.4% |
| Trimagnesium phytate | 3.5% |
| Water | Balance |
| | 100.0% |

A dentifrice was prepared as in Example 3.

EXAMPLES 8-14

| INGREDIENT | Topical pastes for dental use EXAMPLES | | | | | | |
|---|---|---|---|---|---|---|---|
| | 8 | 9 | 10 | 11 | 12 | 13 | 14 |
| | (% by weight) | | | | | | |
| Stannous fluoride | 1.2 | 0.4 | 1.2 | 0.4 | 1.2 | 1.2 | 1.2 |
| Pentasodium phytate | 6.0 | 2.0 | 6.0 | 3.0 | — | — | — |
| Pentapotassium phytate | — | — | — | — | 7.0 | — | — |
| Tricalcium phytate | — | — | — | — | — | 7.0 | — |
| Trimagnesium phytate | — | — | — | — | — | — | 6.0 |
| Propylene glycol | 5.0 | 4.0 | 3.0 | 4.0 | 5.0 | 5.0 | 4.0 |
| Glycerin | 10.0 | 5.0 | 10.0 | 8.0 | 10.0 | 5.0 | 10.0 |
| Sorbitol | — | — | 5.0 | 5.0 | — | 5.0 | 2.0 |
| Hydroxyethyl cellulose | 3.0 | 2.0 | 2.0 | 2.0 | 0.5 | — | 0.5 |
| Xanthan gum | — | 1.0 | 1.0 | 1.0 | 2.0 | 2.5 | 2.5 |
| Flavor | 0.5 | 0.5 | 0.5 | 0.5 | 0.5 | 0.5 | 0.5 |
| Tartaric acid | — | — | — | — | 0.5 | — | — |
| Trisodium citrate dihydrate | — | — | — | — | — | — | 1.0 |
| Butyl parahydroxybenzoate | 0.01 | 0.01 | 0.01 | 0.01 | 0.01 | 0.01 | 0.01 |
| Polyoxyethylene sorbitan monolaurate | 0.5 | 0.5 | 0.5 | 0.5 | 0.5 | 0.5 | 0.5 |
| Saccharin | 0.2 | 0.2 | 0.2 | 0.2 | 0.2 | 0.2 | 0.2 |
| Water | Balance | Balance | Balance | Balance | Balance | Balance | Balance |
| | 100.0 | 100.0 | 100.0 | 100.0 | 100.0 | 100.0 | 100.0 |

Stannous fluoride and phytate were dissolved in 50 parts of water. To prepare a topical paste, this solution was mixed with the solution obtained by dissolving the remaining ingredients in 50 parts of water.

EXAMPLE 15

| Topical solution for dental use | |
|---|---|
| Stannous fluoride | 1.2% |
| Pentasodium phytate | 6.3% |
| Flavor | 0.5% |
| Saccharin | 0.2% |
| Ethanol | 10.0% |
| Water | Balance |
| | 100.0% |

A topical solution for dental use was prepared by adding the above ingredients to water.

EXAMPLE 16

| Topical solution for dental use | |
|---|---|
| Stannous fluoride | 1.2% |
| Pentasodium phytate | 4.5% |
| Trisodium citrate dihydrate | 0.5% |
| Flavor | 0.5% |
| Saccharin | 0.2% |
| Ethanol | 10.0% |
| Water | Balance |
| | 100.0% |

A topical solution was prepared as in Example 15.

EXAMPLE 17

| Desensitizer (liquid) | |
|---|---|
| Stannous fluoride | 0.4% |
| Pentasodium phytate | 3.0% |
| Flavor | 0.5% |
| Saccharin | 0.1% |
| Ethanol | 10.0% |
| Water | Balance |
| | 100.0% |

A solution was prepared as in Example 15.

EXAMPLE 18

| Cavity sealer (liquid) | |
|---|---|
| Stannous fluoride | 1.2% |
| Pentasodium phytate | 6.0% |
| Flavor | 0.25% |
| Saccharin | 0.05% |
| Ethanol | 10.0% |
| Water | Balance |
| | 100.0% |

A solution was prepared as in Example 15.

EXAMPLE 19

| Prophylactic paste | |
|---|---|
| Stannous fluoride | 1.2% |
| Pentasodium phytate | 6.0% |
| Propylene glycol | 3.0% |
| Glycerin | 10.0% |
| Sorbitol | 10.0% |
| Guar gum | 2.0% |
| Zirconium silicate | 50.0% |
| Sodium lauryl sulfate | 1.0% |
| Flavor | 0.5% |
| Saccharin | 0.1% |
| Butyl parahydroxybenzoate | 0.01% |
| Water | Balance |
| | 100.0% |

A paste was prepared as in Example 8.

EXAMPLE 20

| Disintegratable tablet | |
|---|---|
| Stannous fluoride | 4.0 mg |
| Phytic acid | 20 mg |
| Flavor | 10 mg |
| Saccharin | 1 mg |

| Disintegratable tablet | |
| --- | --- |
| Corn starch | 1 g |

The above ingredients were mixed and pressed into a tablet by a usual method.

EXAMPLE 21

| Oral band | |
| --- | --- |
| Stannous fluoride | 300 mg |
| Pentasodium phytate | 1.5 g |
| Sodium carboxymethyl cellulose | 0.5 g |
| Polyvinyl alcohol | 0.5 g |
| Hydroxypropyl cellulose | 9.0 g |
| Polyethylene glycol 4000 | 1.0 g |
| Flavor | 0.05 g |

The above ingredients were dissolved in water to obtain a solution weighing 100 g. The solution was freeze dried to remove the water and formed into a film which is ready for use as an oral band. When applied to teeth, the band becomes tacky due to absorption of water in saliva and firmly adheres to the tooth surface.

EXAMPLES 22–31

| | Mouthwashes (liquid) | | | | | | | | | |
| --- | --- | --- | --- | --- | --- | --- | --- | --- | --- | --- |
| | EXAMPLES | | | | | | | | | |
| INGREDIENT | 22 | 23 | 24 | 25 | 26 (% by weight) | 27 | 28 | 29 | 30 | 31 |
| Stannous fluoride | 0.4 | 0.4 | 0.2 | 0.2 | 0.08 | 0.04 | 0.4 | 0.2 | 0.4 | 0.2 |
| Pentasodium phytate | 4.0 | 2.0 | 1.0 | 0.5 | 0.4 | 0.1 | 3.0 | 2.0 | — | — |
| Pentapotassium phytate | — | — | — | — | — | — | — | — | 3.0 | — |
| Tricalcium phytate | — | — | — | — | — | — | — | — | — | 1.5 |
| Sodium L-ascorbate | — | — | — | 0.8 | 0.8 | — | — | 0.8 | 0.8 | — |
| Citric acid | — | — | 0.2 | — | — | — | 0.3 | — | — | 0.3 |
| Flavor | 0.5 | 0.5 | 0.5 | 0.5 | 0.25 | 0.25 | 0.5 | 0.3 | 0.5 | 0.5 |
| Saccharin | 0.15 | 0.1 | 0.1 | 0.1 | 0.05 | 0.05 | 0.1 | 0.1 | 0.15 | 0.15 |
| Ethanol | 10.0 | 10.0 | 10.0 | 10.0 | 10.0 | 10.0 | 10.0 | 10.0 | 10.0 | 10.0 |
| Water | Balance | Balance | Balance | Balance | Balance | Balance | Balance | Balance | Balance | Balance |
| | 100.0 | 100.0 | 100.0 | 100.0 | 100.0 | 100.0 | 100.0 | 100.0 | 100.0 | 100.0 |

A mouthwash was prepared by dissolving the above ingredients in water.

EXAMPLE 32

| Mouthwash (tablet) | |
| --- | --- |
| STannous fluoride | 0.2 g |
| Pentapotassium phytate | 1.0 g |
| Flavor | 0.2 g |
| Saccharin | 0.05 g |
| Mannitol | 2.0 g |
| Sodium carboxymethyl cellulose | 0.05 g |
| Water | small amount |

The above ingredients were mixed and pressed into a tablet by a usual method. On use, the tablet is dissolved in 100 ml of water and the mouth is washed therewith for 30–60 seconds.

EXAMPLE 33

| Mouthwash (tablet) | |
| --- | --- |
| Stannous fluoride | 0.08 g |
| Phytic acid | 0.4 g |
| Flavor | 0.2 g |
| Saccharin | 0.05 g |
| Gum arabic | 2.0 g |
| Corn starch | 0.5 g |
| Water | small amount |

The above ingredients were mixed and pressed into a tablet by a usual method. On use, the tablet is dissolved in 100 ml of water and the mouth is washed therewith for 30–60 seconds.

What is claimed is:

1. An oral composition for caries prophylaxis comprising stannous fluoride and a phytic acid compound, the content of stannous fluoride being 0.1 to 4% by weight of the total amount of the composition, the content of the phytic acid compound being 0.5 to 10% by weight of the total amount of the composition, the molar ratio of the phytic acid compound to stannous fluoride being in the range of from 0.025:1 to 2.5:1, and the composition being acidic.

2. The oral composition according to claim 1, wherein the composition has a pH of 2 to 6.

3. The oral composition according to claim 2, wherein the composition has a pH of 2 to 5.5.

4. The oral composition according to claim 1, wherein the phytic acid compound is selected from the group consisting of phytic acid, sodium phytate, potassium phytate, lithium phytate, magnesium phytate, calcium phytate, phytin, ammonium phytate, and mixtures thereof.

5. The oral composition according to claim 1, wherein the content of stannous fluoride is 0.3 to 4% by weight of the total amount of the composition and the pH of the composition is 2 to 5.5.

* * * * *